United States Patent [19]

Deguchi et al.

[11] Patent Number: 4,696,894
[45] Date of Patent: Sep. 29, 1987

[54] SILVER HALIDE PHOTOGRAPHIC MATERIALS CONTAINING 1,3,4-THIADIAZOLE DERIVATIVES HAVING A POLAR SUBSTITUENT

[75] Inventors: Naoyasu Deguchi; Tstsuro Kojima; Shigeru Ohno; Koki Nakamura; Hideo Miyazaki, all of Kanagawa, Japan

[73] Assignee: Fuji Photo Film Co., Ltd., Kanagawa, Japan

[21] Appl. No.: 813,198

[22] Filed: Dec. 24, 1985

[30] Foreign Application Priority Data

Dec. 27, 1984 [JP] Japan ................. 59-278856

[51] Int. Cl.$^4$ .................. G03C 1/28; G03C 1/34
[52] U.S. Cl. ................. 430/551; 430/558; 430/611
[58] Field of Search ............. 430/551, 351, 557, 558, 430/611

[56] References Cited

U.S. PATENT DOCUMENTS 4,137,079  1/1979  Houle ............................ 430/611
4,252,895  2/1981  Kato et al. ..................... 430/611
4,451,561  5/1984  Hirabayashi et al. ............. 430/611
4,554,245 11/1985  Hayashi et al. .................. 430/611

Primary Examiner—John L. Goodrow
Attorney, Agent, or Firm—Sughrue, Mion, Zinn, Macpeak, and Seas

[57] ABSTRACT

A silver halide photographic material exhibiting improved interimage effects and having improved sharpness and graininess is disclosed. The material contains at least one compound represented by formula (I) or formula (II):

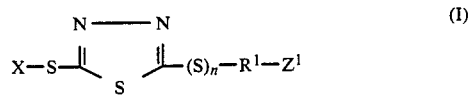

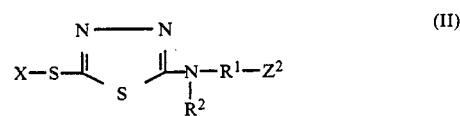

wherein $R^1$ represents a straight or branched chain alkylene, alkenylene or aralkylene group, or an arylene group; $R^2$ represents a hydrogen atom, or a substituted or unsubstituted alkyl, aryl, alkenyl or aralkyl group; X represents a hydrogen atom, an alkali metal atom, an ammonium group or a precursor capable of providing a hydrogen atom or an alkali metal atom under an alkaline condition; $Z^1$ and $Z^2$ each represents a polar group; and n represents 0 or 1.

11 Claims, No Drawings

4,696,894

SILVER HALIDE PHOTOGRAPHIC MATERIALS CONTAINING 1,3,4-THIADIAZOLE DERIVATIVES HAVING A POLAR SUBSTITUENT

FIELD OF THE INVENTION

This invention relates to a silver halide photographic material having improved interimage effects, improved sharpness, and improved graininess.

BACKGROUND OF THE INVENTION

In silver halide color photographic materials, it is well known that color development induces reaction between an oxidized aromatic primary amine color developing agent with a coupler to produce an indophenol dye, an indoaniline dye, an indamine dye, an azomethine dye, a phenoxazine dye, a phenazine dye, or a like dye to thereby form a color image. In this photographic system, color reproduction is generally achieved by a subtractive color process using silver halide emulsions selectively sensitive to each of blue, green, and red light, and yellow-, magenta-, and cyan-dye-forming agents (couplers) that are complementary to the silver halide emulsions, respectively. For example, acylacetanilide and dibenzoylmethane couplers are used for formation of a yellow dye image; pyrazolone, pyrazolobenzimidazole, pyrazolopyrazole, pyrazolotriazole, cyanoacetophenone, and indazolone couplers are typically used for formation of a magenta dye image; and phenol and naphthol couplers are mostly used for formation of a cyan dye image.

Dyes produced by these couplers do not have ideal absorption spectra. In particular, magenta and cyan dyes have disadvantages for color reproduction of color photographic light-sensitive materials, such as a broad absorption spectrum or side abscrption in a short wavelength region.

Side absorption in a short wavelength region tends to cause reduction in saturation. The reduced saturation can be restored to some extent by mainfestation of interimage effects.

Details of interimage effects are described, e.g., in Hanson, et al., *Journal of the Optical Society of America*, Vol. 42, pp. 663–669, A. Thiels, *Zeitschrift fur Wissenschaftliche Photographie, Photophysique und Photo-chemie*, Vol. 47, pp. 106–118 and 246–255.

It has been proposed to obtain favorable interimage effects by introducing diffusible 4-thiazolin-2-thione into a light-exposed color reversal photographic element (U.S. Pat. No. 3,536,486) or an unexposed color reversal photographic element (U.S. Pat. No. 3,563,487).

Japanese Patent Publication No. 34169/73 discloses that remarkable interimage effects can be exerted in a color photographic light-sensitive material by reducing silver halides to silver in the presence of an N-substituted-4-thiazoline-2-thione compound.

Interimage effects obtained by providing a colloidal silver-containing layer between a cyan layer and a magenta layer in a color reversal photographic element are described in *Research Disclosure*, RD No. 13116 (March, 1975).

Furthermore, U.S. Pat. No. 4,082,553 discloses that good interimage effects can be obtained in a color reversal light-sensitive material having a layer structure that allows movement of iodide ions during development, one layer of which contains latent image-forming silver haloiodide grains and another layer of which contains latent image-forming silver halide grains and silver halide grains having their surfaces fogged so that they may be developed irrespective of imagewise exposure.

However, the above-described conventional techniques fail to produce fully satisfactory interimage effects, or the use of a colloidal silver-containing layer or the introduction of fogged silver halide grains brings about a reduction in color density in color reversal light-sensitive materials.

It is also known to produce interimage effects by using a coupler capable of releasing a development inhibitor (i.e., DIR coupler), e.g., a benzotriazole derivative, a mercapto compound, etc., upon reacting with an oxidation product of a color development agent, or using a hydroquinone compound, etc., capable of releasing a development inhibitor, e.g, an iodine ion, a mercapto compound, etc. However, use of these development inhibitor-releasing compounds is accompanied by serious desensitization or reduction of color density and has, therefore, been narrowly limited in its applications.

SUMMARY OF THE INVENTION

An object of this invention is to provide a multi-layer color photographic light-sensitive material which exerts great interimage effects without impairing other photographic properties.

Another object of this invention is to provide a silver halide photographic material having excellent sharpness.

A further object of this invention is to provide a black-and-white silver halide light-sensitive material having high sharpness and excellent graininess.

These objects of this invention can be accomplished by a silver halide photographic material containing at least one compound represented by formula (I) or formula (II)

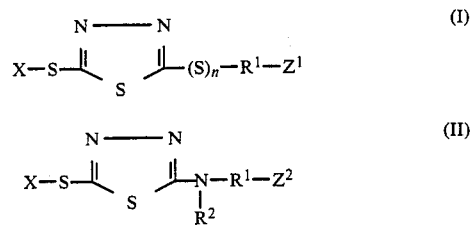

wherein $R^1$ represents a straight or branched chain alkylene, alkenylene or aralkylene group, or an arylene group; $R^2$ represents a hydrogen atom, or a substituted or unsubstituted alkyl, aryl, alkenyl or aralkyl group; X represents a hydrogen atom, an alkali metal atom, an ammonium group, or a precursor capable of providing a hydrogen atom or an alkali metal atom under an alkaline condition; $Z^1$ and $Z^2$ each represents a polar substituent; and n represents 0 or 1.

DETAILED DESCRIPTION OF THE INVENTION

In the above-described formulae (I) and (II), $R^1$ represents a straight chain or branched chain alkylene group, preferably having from 1 to 15 carbon atoms, more preferably from 1 to 10 carbon atoms (e.g., a methylene group, an ethylene group, a propylene group, a butylene group, a hexylene group, a 1- methylethylene group, etc.), a straight chain or branched chain alkenylene group, preferably having from 2 to 15 carbon atoms, more preferably from 2 to 10 carbon atoms (e.g., a vinylene group, a 1-methylvinylene group, etc.), a straight chain or branched chain aralkylene group, preferably having from 7 to 30 carbon atoms, more preferably from 7 to 20 carbon atoms.(e.g., a benzylidene group, etc.) or an arylene group, preferably having from 6 to 30 carbon atoms, more preferably from 6 to 20 carbon atoms (e.g., a phenylene group, a naphthylene group, etc.), with an alkylene group being particularly preferred.

$R^2$ represents a hydrogen atom, a substituted or unsubstituted alkyl group, preferably having from 1 to 10 carbon atoms (e.g., a methyl group, an ethyl group, a propyl group, a 2-dimethylaminoethyl group, etc.), a substituted or unsubstituted aryl group, preferably having from 6 to 20 carbon atoms (e.g., a phenyl group, a 2-methylphenyl group, etc.), a substituted or unsubstituted alkenyl group, preferably having from 2 to 10 carbon atoms (e.g., a propenyl group, a 1-methylvinyl group, etc.) or a substituted or unsubstituted aralkyl group, preferably having from 7 to 15 carbon atoms (e.g., a benzyl group, a phenethyl group, etc.), with a hydrogen atom and an alkyl group being particularly preferred.

X represents a hydrogen atom, an alkali metal atom (e.g., a sodium atom, a potassium atom, etc.), an ammonium group, preferably having from 3 to 30 carbon atoms (e.g., a trimethylammoniumyl chloride group, a dimethylbenzylammoniumyl chloride group, etc.) or a precursor capable of providing a hydrogen atom or an alkali metal atom under an alkaline condition at pH of from 8.5 to 13.5, preferably from 9.0 to 12.5 (e.g., an acetyl group, a cyanoethyl group, a methanesulfonylethyl group, etc.).

The polar substituent as represented by $Z^1$ or $Z^2$ includes, for example, a quaternary ammonium group, preferably having from 3 to 30 carbon atoms (e.g., a trimethylammoniumyl chloride group, a dimethylbenzylammoniumyl chloride group, etc.), an alkoxy group, preferably having from 1 to 15 carbon atoms (e.g., a methoxy group, an ethoxy group, a 2-hydroxyethoxy group, etc.), an alkylthio group, preferably having from 1 to 15 carbon atoms (e.g., a methylthio group, a butylthio group, etc.), an arylthio group, preferably having from 6 to 20 carbon atoms (e.g., a phenylthio group, etc.), a heterocyclic oxy group, preferably having from 1 to 20 carbon atoms (e.g., a 2-pyridyloxy group, a 2-imidazolyloxy group, etc.), a heterocyclic thio group, preferably having from 1 to 20 carbon atoms (e.g., a 2-benzthiazolylthio group, a 4-pyrazolylthio group, etc.), a carbamoyl group, preferably having from 1 to 10 carbon atoms (e.g., an unsubstituted carbamoyl group, a methylcarbamoyl group, etc.), a a sulfamoyl group, preferably having from 0 to 10 carbon atoms (e.g., an unsubstituted sulfamoyl group, a methylsulfamoyl group, etc.), an acyloxy group, preferably having from 2 to 15 carbon atoms (e.g., an acetyloxy group, a benzoyloxy group, etc.), a ureido group, preferably having from 1 to 10 carbon atoms (e.g., an unsubstituted ureido group, a methylureido group, an ethylureido group, etc.), a thioureido group, preferably having from 1 to 10 carbon atoms (e.g., an unsubstituted thioureido group, a methylthioureido group, etc.) and a sulfonyloxy group, preferably having from 1 to 15 carbon atoms (e.g., a methanesulfonyloxy group, a p-toluenesulfonyloxy group, etc.).

$Z^2$ in formula (II) additionally includes a substituted or unsubstituted amino group inclusive of its salt, preferably having from 0 to 10 carbon atoms (e.g., an amino group, an amino hydrochloride group, a methylamino group, a dimethylamino group, a dimethylamino hydrochloride group, a diethylamino group, a diethylamino hydrochloride group, a dibutylamino group, a dipropylamino group, an N-dimethylaminoethyl-N-methylamino group, etc.), an aryloxy group, preferably having from 6 to 20 carbon atoms (e.g., a phenoxy group, etc.), a heterocyclic group, preferably having from 1 to 20 carbon atoms (e.g., a 1-morpholino group, a 1-piperidino group, a 2-pyridyl group, a 4-pyridyl group, a 2-thienyl group a 1-pyrazolyl group, a 2-imidazolyl group, a 2-tetrahydrofuryl group, a tetrahydrothienyl group, etc.) and a cyano group.

Of the groups for $Z^1$ and $Z^2$, a quaternary ammonium group, a carbamoyl group and a ureido group are preferred for $Z^1$ and $Z^2$, and in addition an amino group and a heterocyclic group are preferred for $Z^2$.

In formulae (I) and (II), $Z^1$ and $Z^2$ do not include a sulfonic acid group, a carboxylic acid group, a hydroxy group, or an alkoxycarbonyl group (e.g., a methoxycarbonyl group, an ethoxycarbonyl group, etc.).

The preferred among the compounds of (I) are those wherein n represents 1.

In a black-and-white photographic light-sensitive material according to the present invention comprising two or more silver halide emulsion layers, effects analogues to interimage effects in multi-layer color photographic light-sensitive materials are observed between the two silver halide emulsion layers.

For example, when a black-and-white light-sensitive material comprises a higher sensitive emulsion layer generally having larger silver halide grains and a lower sensitive emulsion layer generally having smaller silver halide grains, the higher sensitive emulsion layer is also developed in a high exposure region where the lower sensitive layer can be developed. In this case, if the compound represented by formula (I) or (II) according to the present invention is incorporated into the higher sensitive layer and/or the lower sensitive layer, the lower sensitive emulsion functions to restrain development of the higher sensitive emulsion in the high exposure region. As a result, the amount of developed silver of the higher sensitive silver halide emulsion generally having larger grains can be decreased to thereby improve graininess in the high exposure region.

Further, according to the present invention, improvements in sharpness can be obtained in both color photographic light-sensitive materials and black-and-white photographic light-sensitive materials, having at least one silver halide emulsion layer.

An intralayer development inhibition effect is also produced simultaneously with the interimage effects (interlayer effects) among different silver halide emulsion layers. This intralayer effect shows itself at the edge between a high exposure region and a low exposure region in each silver halide emulsion layer (edge effect).

If at least one of the compounds of formula (I) or formula (II) is incorporated into the silver halide emulsion layer, inhibition on development works at the edge from the high exposure region to the low exposure region. This development inhibition at the edge makes the edge clearer and thus improves sharpness.

Specific examples of the compounds represented by formula (I) and formula (II) according to the present invention are shown below, but they are not deemed to limit the compounds of this invention.
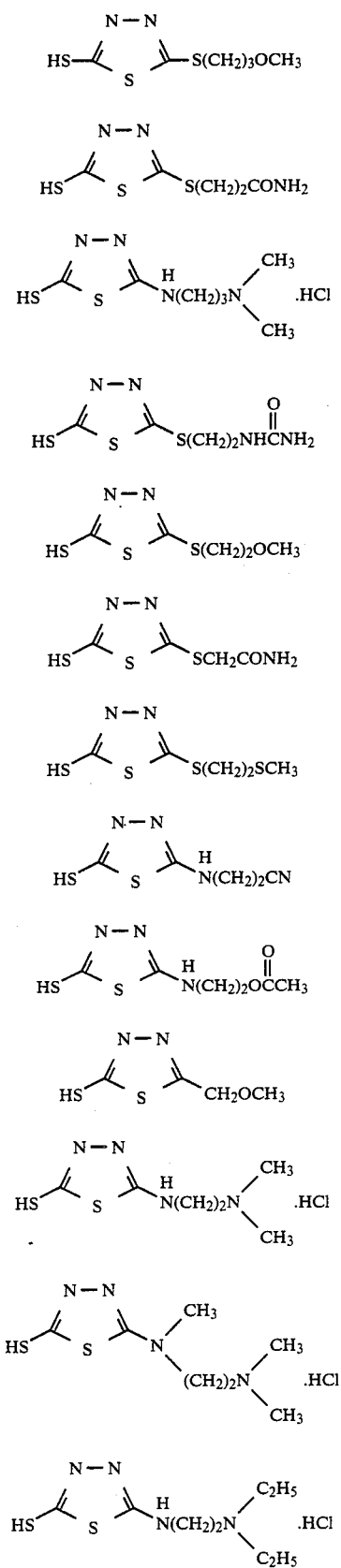
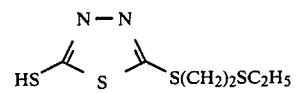
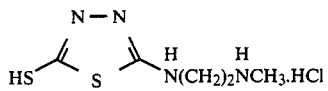
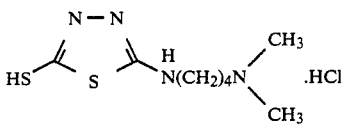
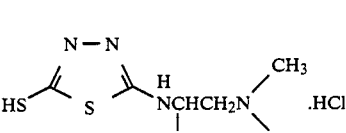
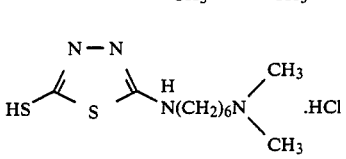
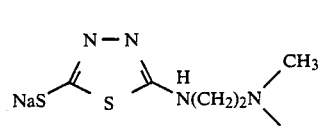
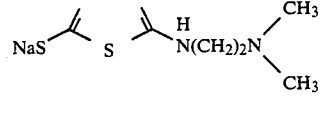
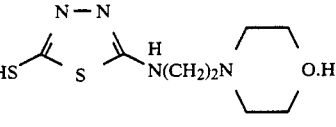
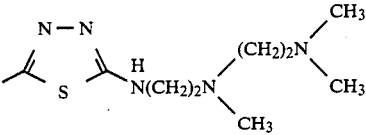
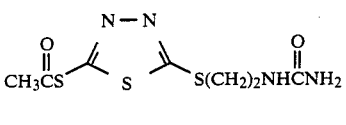
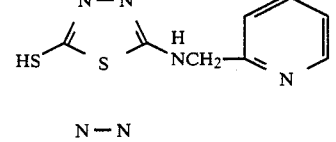
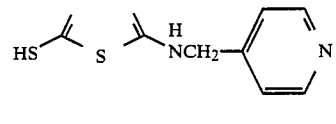
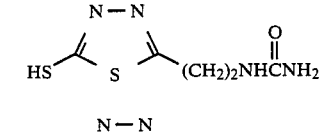
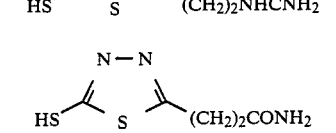

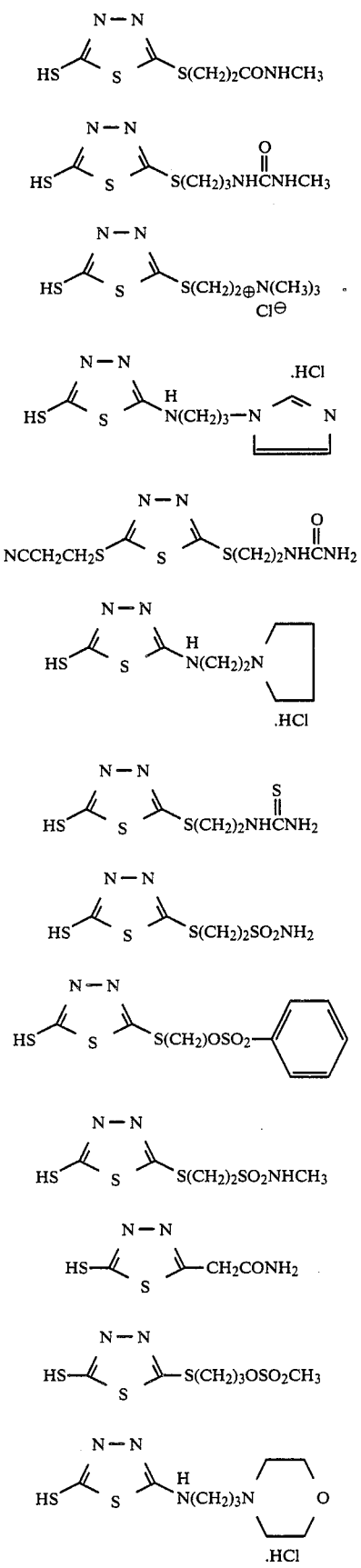

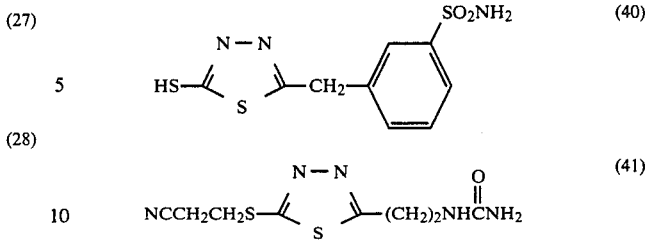

(27)

(28)

(29)

The compounds of formula (I) or (II) which can be used in the present invention can be synthesized by the process described in *Advances in Heterocyclic Chemistry*, Vol. 9, pp. 165–209 (1968).

Typical examples of synthesis are shown below.

SYNTHESIS EXAMPLE 1

Synthesis of Compound (2)

To 300 ml of acetone was added 15 g of 2,5-dimercapto-1,3,4-thiadiazole, and 22 ml of a 28% sodium methoxide solution and 12 g of ε-chloropropionamide were added thereto. To the mixture was further added 15 g of sodium iodide, followed by heat-refluxing for 20 hours. After cooling, the crystals formed were filtered, washed with water and recrystallized from a mixed solvent of dimethylformamide and methanol to obtain 12.0 g of Compound (2) having a melting point of from 175° to 177° C.

SYNTHESIS EXAMPLE 2

Synthesis of Compound (4)

In 100 ml of ethanol were dissolved 15.0 g of 2,5-dimercapto-1,3,4-thiadiazole and 20 ml of a 28% sodium methoxide solution under heating. To the resulting solution was added dropwise 13.5 g of 2-chloroethylurea. After the dropwise addition, the reaction mixture was heated under reflux for 4 hours. The reaction mixture was then poured into 700 ml of ice-water, and the precipitated crystals were filtered and recrystallized from methanol to provide 16.4 g of Compound (4) having a melting point of from 174° to 176° C.

SYNTHESIS EXAMPLE 3

Synthesis of Compound (3)

To 150 ml of ethanol was added 17.6 g of 1-(3-dimethylaminopropyl)thiosemicarbazide, and 7.9 g of potassium hydroxide was dissolved therein. Then, 34.3 g of carbon disulfide was added thereto dropwise at room temperature, followed by heating under reflux for 5 hours. After cooling, the crystals formed were filtered and recrystallized from methanol and concentrated hydrochloric acid to obtain 11.3 g of Compound (3) having a melting point of from 204° to 205° C.

SYNTHESIS EXAMPLE 4

Synthesis of Compound (5)

In 200 ml of ethanol were dissolved 30.0 g of 2,5-dimercapto-1,3,4-thiadiazole and 40 ml of a 28% sodium methoxide solution under heating, and 20.8 g of methoxyethyl chloride was added dropwise to the solution. After the dropwise addition, the mixture was refluxed for 2 hours. After completion of the reaction, the reaction mixture was filtered, and the filtrate was dried under reduced pressure to a solid, which was then recrystallized from ethyl acetate and n-hexane to obtain 29.8 g of Compound (5) having a melting point of from 59° to 60° C.

SYNTHESIS EXAMPLE 5

Synthesis of Compound (7)

In 100 ml of ethanol were dissolved 10.5 g of 2,5-dimercapto-1,3,4-thiadiazole and 14 ml of a 28% sodium methoxide solution under heating, and 8.5 g of methylthioethyl chloride was then added thereto dropwise. After the addition, the mixture was heated under reflux for 3 hours. After completion of the reaction, the reaction mixture was poured into 1 liter of ice-water, and the precipitated crystals were filtered and recrystallized from ethyl acetate and n-hexane to provide 8.6 of Compound (7) having a melting point of from 75° to 76° C.

SYNTHESIS EXAMPLE 6

Synthesis of Compound (29)

In 100 ml of n-butanol were dissolved 15.0 g of 2,5-dimercapto-1,3,4-thiadiazole and 17.4 g of 2-chloroethyltrimethylammonium chloride under heating, and 7.8 ml of pyridine was then dropwise added thereto, followed by heating under reflux for 3 hours. After completion of tne reaction, tne precipitated crystals were filtered and recrystallized from methanol to obtain 18.1 g of Compound (29) having a melting point of from 222° to 225° C.

In multi-layer color photographic light-sensitive materials to which the present invention is applied, the compound of formula (I) or (II) is incorporated into at least one silver halide emulsion layer or a layer adjacent thereto, such as a yellow filter layer, an antihalation layer, an intermediate layer, a protective layer, etc. Preferably, the compound is incorporated in a silver halide emulsion layer.

In black-and-white photographic light-sensitive materials to which the present invention is applied, the compound of formula (I) or (II) is incorporated in a silver halide emulsion layer and/or a protective layer.

The amount of the compound (I) or (II) to be added varies depending on the properties, end use, and/or method of development of the silver halide photographic materials to be used, but, in general, preferably ranges from $10^{-1}$ to $10^{-5}$ mols, and more preferably from $3\times10^{-2}$ to $3\times10^{-4}$ mols, per mol of silver halide in the layer in which the compound is incorporated or in layers adjacent thereto when silver halide is not contained in the layer in which the compound is incorporated.

The compound of formula (I) or (II) can be incorporated into the light-sensitive material by dissolving it in a solvent commonly employed in photographic light-sensitive materials, such as water, methanol, ethanol, propanol, a fluorinated alchol, etc., and adding the solution to a hydrophilic colloid. Addition to a silver halide emulsion layer may be effected at any stage selected depending upon the end use, e.g., during grain formation of a silver halide emulsion, during physical ripening, immediately before, during or after chemical sensitization, or at the time of preparing a coating composition.

Light-sensitive materials to which the present invention can be applied include, for example, color photographic light-sensitive materials, such as color negative films, color reversal films (either coupler-in-emulsion type or coupler-in-developer type), color papers, color positive films, color reversal papers, color diffusion transfer materials, dye transfer materials, etc.; and black-and-white photographic light-sensitive materials, such as black-and-white negative films, black-and-white photographic papers, X-ray films, lith films, etc.

Binders or protective colloids which can be used in emulsion layers or intermediate layers of light-sensitive materials include gelatin to advantage, but other hydrophilic colloids may also be employed alone or in combination with gelatin.

Gelatin to be used in the present invention may be either lime-processed or acid-processed. Details for gelatin preparation are described, for example, in Arthur Veis, *The Macromolecular Chemistry of Gelatin*, Academic Press (1964).

In photographic emulsion layers, any of silver bromide, silver iodobromide, silver iodochlorobromide, silver chlorobromide and silver chloride may be employed. In particular, good results can be obtained when at least one photographic emulsion layer contains silver chloroiodobromide, silver iodobromide, or silver chloroiodide having an iodine content of from 0.5 to 15 mol %.

A mean grain size of silver halide grains in the photographic emulsion (the grain size being defined as a grain diameter if the grain has a spherical or a nearly spherical form and as a length of the edge if the grain has a cubic form, and being averaged based on projected areas of the grains) is not particularly restricted, but is preferably 3 μm or less.

Grain size distribution may be either narrow or broad.

Silver halide grains in the photographic emulsion may have a regular crystal form, such as a cube and an octahedron, an irregular crystal form, such as a sphere and a plate-like (tabular), or a composite form thereof. Further, silver halide grains may be a mixture of grains having various crystal forms.

An emulsion wherein tabular silver halide grains having a diameter 5 times the thickness thereof occupy 50% or more of the total projection area may also be employed.

The individual silver halide grains may comprise a core and an outer shell or may be homogeneous. Further, they may be either those grains where a latent image is predominantly formed on the surface thereof or those grains where a latent image is predominantly formed in the interior thereof.

Photographic emulsions which can be used in the present invention can be prepared according to conventional methods as described, for example, in P. Glafkides, *Chiemie et Physique Photographique*, Paul Montel (1967); G. F. Duffin, *Photographic Emulsion Chemistry*, Focal Press (1966), V. L. Zelikman et al., *Making and Coating Photographic Emulsion*, Focal Press (1964), etc. In more detail, photographic emulsions can be prepared according to any of the acid process, the neutral process, the ammonia process, and the like. Methods for reacting a water-soluble silver salt with a water-soluble halide include a single jet method, a double jet method, a combination thereof, and the like.

A method in which silver halide grains are produced in the presence of excess silver ions (the so-called reverse mixing method) can also be used. Further, the so-called controlled double jet method, in which the pAg of the liquid phase wherein silver halide grains are to be precipitated is maintained constant, can also be employed. According to this method, silver halide emulsions in which grains have a regular crystal form and a substantially uniform size distribution can be obtained.

Two or more silver halide emulsions prepared separately may be employed in the form of a mixture.

In a process of producing silver halide grains or physically ripening the silver halide grains, cadmium salts, zinc salts, lead salts, thallium salts, iridium salts or complex salts thereof, rhodium salts or complex salts thereof, iron salts or complex salts thereof, and the like may be present.

Typically, the silver halide emulsion is chemically sensitized. Chemical sensitization can be carried out by processes as described, e.g., in H. Frieser (ed.), *Die Grundlagen der Photographischen Prozesse mit Silberhalogeniden*, Akademische Verlagsgesellschaft, pp. 675-734 (1968).

More specifically, chemical sensitization can be carried out by sulfur sensitization using a compound containing sulfur capable of reacting with active gelatin or silver ions (e.g., thiosulfates, thioureas, mercapto compounds, rhodanines, etc.), reduction sensitization using a reducing material (e.g., stannous salts, amines, hydrazine derivatives, formamidinesulfinic acid, silane compounds, etc.), noble metal sensitization using a noble metal compound (e.g., gold complex salts, and complex salts of Periodic Table Group VIII metals, e.g., Pt, Ir, Pd, etc.) or a combination thereof.

The photographic emulsions to be used in the present invention can contain various compounds for the purpose of preventing fog in the preparation, preservation, or photographic processing, or for stabilizing photographic properties. Examples of such compounds include azoles, such as benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, aminotriazoles, benzotriazoles, nitrobenzotriazoles, mercaptotetrazoles (particularly 1-phenyl-5-mercaptotetrazole), etc.; mercaptopyrimidines; mercaptotriazines; thioketo compounds, such as oxazolinethione, etc.; azaindens, such as triazaindenes, tetraazaindenes (particularly, 4-hydroxy-substituted-(1,3,3a,7)tetraazaindenes), pentaazaindenes, etc.; benzenethiosulfonic acid; benzenesulfinic acid; benzenesulfonic acid amide; and many other compounds known as antifoggants or stabilizers.

Photographic emulsion layers or other hydrophilic colloidal layers of the light-sensitive materials prepared according to the present invention may contain a wide variety of surface active agents for various purposes, for example, as a coating aid or for prevention of static charge, improvement of slipperiness, as a dispersing agent, for prevention of adhesion, improvement of photographic characteristics (e.g., acceleration of development, increase in contrast, sensitization, etc.), and the like.

For the purpose of increasing sensitivity or contrast or acceleration of development, the photographic emulsion of the light-sensitive materials in accordance with the present invention may contain, for example, polyalkylene oxides or derivatives thereof, e.g., ethers, esters and amines, thioether compounds, thiomorpholines, quaternary ammonium salt compounds, urethane derivatives, urea derivatives, imidazole derivatives, 3-pyrazolidones, and the like.

The photographic emulsion layers or other hydrophilic colloidal layers of the light-sensitive materials of the present invention may further contain a dispersion of a water-insoluble or sparingly water-soluble synthetic polymer for the purpose of improving dimensional stability or the like. Examples of such a polymer includes those comprising, as a monomer component, one or more of alkyl (meth)acrylates, alkoxyalkyl (meth)acrylates, glycidyl (meth)acrylate, (meth)acrylamide, vinyl esters (e.g., vinyl acetate), acrylonitrile, olefins and styrene, or a combination of these monomer components and acrylic acid, methacrylic acid, $\alpha,\beta$-unsaturated dicarboxylic acids, hydroxyalkyl (meth)acrylates, sulfoalkyl (meth)acrylates, styrenesulfonic acid, etc.

The photographic emulsions which can be used in the present invention may be spectrally sensitized with methine dyes or others. Dyes to be used include cyanine dyes, merocyanine dyes, complex cyanine dyes, complex merocyanine dyes, holopolar cyanine dyes, hemicyanine dyes, styryl dyes and hemioxonol dyes, with cyanine dyes, merocyanine dyes and complex merocyanine dyes being particularly useful. Any nucleus conventionally employed in cyanine dyes as a basic heterocyclic nucleus may be applied to these dyes. Examples of such nuclei include a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus, etc.; the above-described nuclei to which an alicyclic hydrocarbon ring is fused; and the above-described nuclei to which an aromatic hydrocarbon ring is fused, e.g., an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus, a quinoline nucleus, etc. These nuclei may have a substituent on their carbon atoms.

The merocyanine dyes or complex merocyanine dyes may have a 5- to 6-membered heterocyclic nucleus having a ketomethylene structure, e.g., a pyrazolin-5-one nucleus, a thiohydantoin nucleus, a 2-thiooxazolidine-2,4-dione nucleus, a thiazolidine-2,4-dione nucleus, a rhodanine nucleus, a thiobarbituric acid nucleus, etc.

These sensitizing dyes may be used either individually or in combinations thereof. Combinations of sensitizing dyes can be desirably employed for the purpose of supersensitization.

The photographic emulsion may further contain, in combination with the sensitizing dye, a substance which neither exhibits spectral sensitizing activity per se nor substantially absorbs visible light, but which shows supersensitizing activity, when used together with the sensitizing dye. Examples of such substances are aminostyryl compounds substituted with a nitrogen-containing heterocyclic group (U.S. Pat. Nos. 2,933,390 and 3,635,721), aromatic organic acidformaldehyde condensates (U.S. Pat. No. 3,743,510), cadmium salts, azaindene compounds, and the like.

The present invention is applicable to multi-layer multicolor photographic materials having at least two layers being different in spectral sensitivity. Multi-layer neutral color photographic materials usually comprise a support having provided thereon at least one red-sensitive emulsion layer, at least one green-sensitive emulsion layer and at least one blue-sensitive emulsion layer. The order of these layers may arbitrarily be selected according to the intended purpose. For natural color reproduction, typically the red-sensitive emulsion layer contains a cyan-forming coupler, the green-sensitive emulsion layer contains a magenta-forming coupler, and the blue-sensitive emulsion layer contains a yellow-forming coupler. However, other combinations may also be employed, if desired.

Photographic emulsion layers or light-insensitive layers of the photographic light-sensitive materials according to the present invention may contain color forming couplers, i.e., compounds capable of developing a color upon oxidative coupling with an aromatic primary amine developing agent (e.g., phenylenediamine derivatives or aminophenol derivatives) in color development processing. Examples of such couplers include 5-pyrazolone couplers, pyrazolobenzimidazole couplers, pyrazolotriazole couplers, pyrazoloimidazole couplers, pyrazolopyrazole couplers, pyrazolotriazole couplers, pyrazolotetrazole couplers, cyanoacetylcumarone couplers, open-chain acylacetonitrile couplers, etc., as magenta couplers; acylacetamide couplers (e.g., benzoyl acetanilides, pivaloylacetanilides, etc.) as yellow couplers; and naphthol couplers, phenol couplers, etc., as cyan couplers. It is desirable that these couplers have a hydrophobic group called ballast group in their molecule and are thereby non-diffusible or they have a polymerized form. These couplers may be either 4-equivalent or 2-equivalent to silver ions. In addition to these couplers, colored couplers having a color correcting effect or couplers capable of releasing a development inhibitor with the progress of development (so-called DIR couplers) may also be used.

Moreover, colorless DIR coupling compounds which produce a colorless product upon coupling reaction and release a development inhibitor may also be used. Further, other compounds capable of releasing a development inhibitor with the progress of development may be used.

In order to satisfy various requirements demanded for light-sensitive materials, the above-described couplers and the like can be incorporated into two or more different layers, or two or more of these couplers and the like may be incorporated into the same layer.

Couplers can be incorporated into silver halide emulsion layers by known processes, e.g., the process disclosed in U.S. Pat. No. 2,322,027. For example, the coupler is dissolved in a high boiling organic solvent, such as an alkyl phthalate (e.g., dibutyl phthalate, dioctyl phthalate, etc.), a phosphoric ester (e.g., diphenyl phosphate, triphenyl phosphate, tricresyl phosphate, dioctylbutyl phosphate, etc.), a citric ester (e.g., tributyl acetylcitrate, etc.), a benzoic ester (e.g., octyl benzoate, etc.), an alkylamide (e.g., diethyllauryamide, etc.), a fatty acid ester (e.g., dibutoxyethyl succinate, diethyl azelate, etc.), a trimesic ester (e.g., tributyl trimesate, etc.), and the like, or a low boiling organic solvent having a boiling point of from about 30° to 150° C., e.g., a lower alkyl acetate, ethyl propionate, sec-butyl alcohol, methyl isobutyl ketone, β-ethoxyethyl acetate, methyl cellosolve acetate, etc., or a mixture of the high boiling organic solvent and the low boiling organic solvent, and the resulting coupler solution is then dispersed in a hydrophilic colloid.

Couplers may also be incorporated into silver halide emulsion layers by a dispersion process using a polymer as described in Japanese Patent Publication No. 39853/76 and Japanese Patent Application (OPI) No. 59943/76.

Couplers having an acid group, e.g., a carboxyl group or a sulfo group, can be introduced in a hydrophilic colloid as an alkaline aqueous solution.

The photographic light-sensitive materials according to the present invention can contain an organic or inorganic hardener in the emulsion layers or other hydrophilic colloidal layers. Examples of the hardener to be used include chromium salts (e.g., chromium alum, chromium acetate, etc.), aldehydes (e.g., formaldehyde, glyoxal, glutaraldehyde, etc.), N-methylol compounds (e.g., dimethylolurea, methyloldimethylhydantoin, etc.), dioxane derivatives (e.g., 2,3-dihydroxydioxane, etc.), active vinyl compounds (e.g., 1,3,5-triacryloyl-hexahydro-s-triazine, 1,3-vinylsulfonyl-2-propanol, etc.), active halogen compounds (e.g., 2,4-dichloro-6-hydroxy-s-triazine, etc.), mucohalogenic acids (e.g., mucochloric acid, mucophenoxychloric acid, etc.), either alone or in combinations thereof.

In the light-sensitive materials prepared by the present invention, when a hydrophilic colloidal layer contains a dye or an ultraviolet absorbent, such may be mordanted with a cationic polymer.

The light-sensitive materials prepared by the present invention may contain a color fog preventing agent, such as hydroquinone derivatives, aminophenol derivatives, gallic acid derivatives, ascorbic acid derivatives, and the like.

The hydrophilic colloidal layers of the light-sensitive materials of this invention may contain an ultraviolet absorbent, such as a benzotriazole compound substituted with an aryl group (e.g., those described in U.S. Pat. No. 3,533,794), a 4-thiazolidone compound (e.g., those described in U.S. Pat. Nos. 3,314,794 and 3,352,681), a benzophenone compound (e.g., those described in Japanese Patent Application (OPI) No. 2784/71), a cinnamic acid ester compound (e.g., those described in U.S. Pat. Nos. 3,705,805 and 3,707,375), a butadiene compound (e.g., those described in U.S. Pat. No. 4,045,229) and a benzoxazole compound (e.g., those described in U.S. Pat. No. 3,700,455). Ultraviolet absorbing couplers (e.g., α-naphthol type cyan color forming couplers) or ultraviolet absorbing polymers may be used as ultraviolet absorbents. These ultraviolet absorbents may be mordanted or fixed to a specific layer.

The hydrophilic colloidal layer of the light-sensitive materials of the present invention may contain water-soluble dyes as filter dyes or for prevention of irradiation or for various other purposes. Such water-soluble dyes include oxonol dyes, hemioxonol dyes, styryl dyes, merocyanine dyes, cyanine dyes and azo dyes, with oxonol dyes, hemioxonol dyes, and merocyanine dyes being particularly useful.

In carrying out the present invention, the following known discoloration inhibitors may be used. Further, color image stabilizing agents may be used individually or in a combination of two or more thereof. The known discoloration inhibitors include hydroquinone derivatives, gallic acid derivatives, p-alkoxyphenols, p-oxyphenol derivatives and bisphenols.

The light-sensitive materials according to the present invention can be processed by known processes with known processing solutions as described, e.g., in *Research Disclosure* RD No. 176, pp. 28–30 (Dec., 1978). The processing temperature is usually selected from 18° to 50° C., but lower or higher temperatures may also be employed.

In photographic processing, the silver halide photographic materials of the present invention are subjected to black-and-white development, followed by fixing, in the case of black-and-white light-sensitive materials; or color development, bleaching and fixing in the case of color light-sensitive materials; or black-and-white development, reversal, color development, bleaching, followed by fixing in the case of color reversal light-sensitive materials.

A first developer to be used in the present invention can contain a known developing agent. Examples of known developing agents include dihydroxybenzenes (e.g., hydroquinone), 3-pyrazolidones (e.g., 1-phenyl-3-pyrazolidone), aminophenols (e.g., N-methyl-p-aminophenol), 1-phenyl-3-pyrazolines, ascorbic acid, a heterocyclic compound having a skeleton like condensed 1,2,3,4-tetrahydroquinoline ring and indolene ring as disclosed in U.S. Pat. No. 4,067,872, and the like. These developing agents may be used alone or in combinations thereof.

The black-and-white developer which can be used in the present invention can contain, if desired, preservatives (e.g., sulfites, bisulfites, etc.), buffering agents (e.g., carbonates, boric acid, borates, alkanolamines, etc.), alkali agents (e.g., hydroxides, carbonates, etc.), dissolution aids (e.g., polyethylene glycols or esters thereof, etc.), pH-adjusters (e.g., acetic acid or like organic acids), sensitizers (e.g., quaternary ammonium salts), development accelerators, surface active agents, toning agents, defoaming agents, hardeners, viscosity-imparting agents, and the like.

The first developer should contain a compound which functions as a silver halide solvent but, usually, the above-described sulfites added as preservatives can serve as silver halide solvents. Specific examples of these sulfites and other employable silver halide solvents include KSCN, NaSCN, $K_2SO_3$, $Na_2SO_3$, $K_2S_2O_5$, $Na_2S_2O_5$, $K_2S_2O_3$, $Na_2S_2O_3$, etc.

A development accelerator is used for imparting a development accelerating property to the developer. In particular, one or more compounds that may be used either alone or in combination with the above-described silver halide solvent are those represented by formula (A)

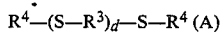

$$R^4-(S-R^3)_d-S-R^4 \quad (A)$$

wherein $R^3$ represents an alkylene group having from 2 to 10 carbon atoms which may contain an ether linkage; $R^4$ represents a substituted or unsubstituted alkyl group having from 2 to 10 carbon atoms which may contain an ether linkage or an ester linkage, and d represents 0 or an integer of from 1 to 3.

Addition of too small an amount of these silver halide solvents retards development progress, while addition of too large an amount generates fog in the silver halide emulsion. Accordingly, there is naturally set a preferred range of the amount of the silver halide solvent to be used, which can readily determined by the one skilled in the art.

For example, it is preferable to use $SC^\ominus$ in an amount ranging from 0.005 to 0.02 mol, and more preferably from 0.01 to 0.015 mol, per liter of developer; and to use $SO_3^{2\ominus}$ in an amount ranging from 0.05 to 1 mol and more preferably from 0.1 to 0.5 mol, per liter of developer.

The compound represented by formula (A), when added to a black-and-white developer, is preferably used in an amount of from $5 \times 10^{-6}$ to $5 \times 10^{-1}$ mol, and more preferably from $1 \times 10^{-4}$ to $2 \times 10^{-1}$ mol, per liter of a developer.

The thus prepared developer is adjusted to have such a pH value sufficient to provide desired density and contrast, preferably between about 8.5 and about 11.5

A fogging bath (reversing bath) which can be used in a reversal process can contain a known fogging agent, such as stannous ion complex salts, e.g., a stannous ion-organic phosphoric acid complex salt (U.S. Pat. No. 3,617,282), a stannous ion-organic phosphonocarboxylic acid complex salt (Japanese Patent Publication No. 32616/81), a stannous ion-aminopolycarboxylic acid complex salt (British Patent No. 1,209,050), etc., and boron compounds, e.g., a boron hydride compound (U.S. Pat. No. 2,984,567), a heterocyclic amine-boran compound (British Pat. No. 1,011,000), etc. Such a fogging bath has a broad range of pH over an acid to alkali side, i.e., from 2 to 12, preferably from 2.5 to 10, and more preferably from 3 to 9.

A color developer which can be used in the present invention has a composition generally employed as a color developer, which contains an aromatic primary amine developing agent. Preferred examples of the aromatic primary amine color developing agent are p-phenylenediamine derivatives, e.g., N,N-diethyl-p-phenylenediamine, 2-amino-5-diethylaminotoluene, 2-amino-5-(N-ethyl-N-laurylamino)toluene, 4-[N-ethyl-N-(β-hydroxyethyl)amino]aniline, 2-methyl-4-[N-ethyl-N-(βhydroxyethyl)amino]aniline, N-ethyl-N-(β-methanesulfoamidoethyl)-3-methyl-4-aminoaniline, N-(2-amino-5-diethylaminophenylethyl)methanesulfonamide, N,N-dimethyl-p-phenylenediamine, and 4-amino-3-methyl-N-ethyl-N-methoxyethylaniline, 4-amino-3-methyl-N-ethyl-N-β-ethoxyethylaniline and 4-amino-3-methyl-N-ethyl-N-β-butoxyethylaniline or salts thereof (e.g., sulfates, hydrochlorides, sulfites, p-toluenesulfonates, etc.) disclosed in U.S. Pat. Nos. 3,656,950 and 3,698,525, and the like.

The color developer can contain other known developer components. For example, one or a combination of sodium hydroxide, potassium hydroxide, sodium carbonate, potassium carbonate, sodium tertiary phosphate, potassium tertiary phosphate, potassium metaborate, borax, etc. can be added as an alkali agent or buffer agent.

The color developer can also contain a preservative, such as a sulfite (e.g., sodium sulfite, potassium sulfite, potassium bisulfite, sodium bisulfite, etc.) and hydroxylamine.

The color developer can further contain, if desired, an optional development accelerator. Examples of the accelerator include various pyridinium compounds and other cationic compounds, cationic dyes, e.g., phenosafranine, etc., and neutral salts, e.g., thallium nitrate, potassium nitrate, etc., as typically described in U.S. Pat. No. 2,648,604, Japanese Patent Publication No. 9503/69, and U.S. Pat. No. 3,671,247; nonionic compound pounds, such as polyethylene glycol or its derivatives, polythioethers, etc., as described in Japanese Patent Publication No. 9504/69 and U.S. Pat. Nos. 2,533,990, 2,531,832, 2,950,970, and 2,577,127; organic solvents, organic amines, ethanolamine, ethylenediamine, diethanolamine, etc. as described in Japanese Patent Publication No. 9509/69 and Belgian Pat. No. 682,862; and compounds as described in L. F. A. Mason, *Photographic Processing Chemistry*, pp. 40–43, Focal Press (1966).

The color developer can furthermore contain a water softener, such as aminopolycarboxylic acids, e.g., ethylenediaminetetraacetic acid, nitrilotriacetic acid, cyclohexanediaminetetraacetic acid, imidinoacetic acid, N-hydroxymethylethylenediaminetriacetic acid, diethylenetriaminepentaacetic acid, etc.

The color developer may contain a competitive coupler, e.g., citrazinic acid, J-acid, H-acid, etc., or a compensating developing agent, such as p-aminophenol, N-benzyl-p-aminophenol, 1-phenyl-3-pyrazolidone, etc.

The color developer preferably has a pH of from about 8 to 13. The temperature of the color developer is usually selected from 20° to 70° C., and preferably from 30° to 60° C.

The photographic emulsion after color development is usually subjected to bleaching. Bleaching may be carried out simultaneously with fixing, or these two processes may be carried out separately. Examples of bleaching agents to be used include compounds of polyvalent metals, e.g., iron(III), cobalt(IV), chromium(VI), copper(II), etc., peracids, quinones, nitroso compounds, and the like. Specific examples of these bleaching agents are ferricyanides; bichromates; complex salts of iron-(III) or cobalt(III) with aminopolycarboxylic acids, e.g., ethylenediaminetetraacetic acid, nitrilotriacetic acid, 1,3-diamino-2-propanoltetraacetic acid, etc., or organic acids, e.g., citric acid, tartaric acid, malic acid, etc.; persulfates; permanganates; nitrophenol; and the like. Of these, potassium ferricyanide, sodium ethylenediaminetetraacetato ferrate(III) and ammonium ethylenediaminetetraacetato ferrate(III) are particularly useful. Aminopolycarboxylic acid iron(III) complex salts are useful in both an independent bleaching solution and a combined bleach-fix bath.

The bleaching or bleach-fix bath can contain a bleach accelerating agent and other various additives as described in U.S. Pat. Nos. 3,042,520 and 3,241,966, Japanese Patent Publication Nos. 8506/70 and 8836/70.

A fixer to be used in the present invention contains from about 30 to 200 g/l of ammonium thiosulfate, sodium thiosulfate or pottasium thiosulfate as a fixing agent and can further contain a stabilizer, e.g., sulfites, metabisulfites, etc.; a hardener, e.g., potassium alum, etc.; a pH buffer, e.g., acetates, borates, phosphates, carbonates, etc.; and the like. The fixer has a pH of from 3 to 10, and preferably from 5 to 9.

The present invention will now be illustrated in greater detail with reference to the following examples, but it should be understood that the present invention is not limited thereto.

EXAMPLE 1

A multi-layer color light-sensitive material was prepared by coating the following layers on a cellulose triacetate film support in the order listed.

| First Layer: (Antihalation Layer) | |
|---|---|
| A gelatin layer containing: | |
| Black colloidal silver | 0.18 g/m$^2$ |
| Second Layer: (Intermediate Layer) | |
| A gelatin layer containing: | |
| 2,5-Di-t-pentadecylhydroquinone | 0.18 g/m$^2$ |
| Coupler C-3 | 0.11 g/m$^2$ |
| Third Layer: (First Red-Sensitive Emulsion Layer) | |
| A gelatin layer containing: | |
| Silver iodobromide emulsion (silver iodide: 4 mol %, mean grain size: 0.4 μm) | 0.72 g-Ag/m$^2$ |
| Sensitizing Dye A | 9.0 × 10$^{-5}$/mol per mol of Ag |
| Sensitizing Dye B | 3.0 × 10$^{-5}$ mol per mol of Ag |
| Sensitizing Dye C | 4.2 × 10$^{-4}$ mol per mol of Ag |
| Sensitizing Dye D | 3.0 × 10$^{-5}$ mol per mol of Ag |
| Coupler C-4 | 0.093 g/m$^2$ |
| Coupler C-5 | 0.31 g/m$^2$ |
| Coupler C-6 | 0.01 g/m$^2$ |
| Fourth Layer: (Second Red-Sensitive Emulsion Layer) | |
| A gelatin layer containing: | |
| Silver iodobromide emulsion (silver iodide: 10 mol %; mean grain size: 1.0 μm) | 1.2 g-Ag/m$^2$ |
| Sensitizing Dye A | 7.8 × 10$^{-5}$ mol per mol of Ag |
| Sensitizing Dye B | 2.2 × 10$^{-5}$ mol per mol of Ag |
| Sensitizing Dye C | 3.0 × 10$^{-4}$ mol per mol of Ag |
| Sensitizing Dye D | 2.2 × 10$^{-5}$ mol per mol of Ag |
| Coupler C-4 | 0.1 g/m$^2$ |
| Coupler C-5 | 0.061 g/m$^2$ |
| Coupler C-7 | 0.046 g/m$^2$ |
| Fifth Layer: (Third Red-Sensitive Emulsion Layer) | |
| A gelatin layer containing: | |
| Silver iodobromide emulsion (silver iodide: 10 mol %; mean grain size: 1.5 μm) | 1.5 g-Ag/m$^2$ |
| Sensitizing Dye A | 8.0 × 10$^{-5}$ mol per mol of Ag |
| Sensitizing Dye B | 2.4 × 10$^{-5}$ mol per mol of Ag |
| Sensitizing Dye C | 3.3 × 10$^{-5}$ mol per mol of Ag |
| Sensitizing Dye D | 2.4 × 10$^{-5}$ mol per mol of Ag |
| Coupler C-7 | 0.32 g/m$^2$ |
| Coupler C-16 | 0.001 g/m$^2$ |
| Sixth Layer: (Intermediate Layer) | |
| A gelatin layer. | |
| Seventh Layer: (First Green-Sensitive Emulsion Layer) | |
| A gelatin layer containing: | |
| Silver iodobromide emulsion (silver iodide: 5 mol %; mean grain size: 0.5 μm) | 0.55 g-Ag/m$^2$ |
| Sensitizing Dye G | 3.8 × 10$^{-4}$/mol per mol of Ag |
| Sensitizing Dye E | 1.5 × 10$^{-4}$ mol per mol of Ag |
| Coupler C-8 | 0.29 g/m$^2$ |
| Coupler C-3 | 0.04 g/m$^2$ |
| Coupler C-9 | 0.055 g/m$^2$ |
| Coupler C-10 | 0.058 g/m$^2$ |
| Eighth Layer: (Second Green-Sensitive Emulsion Layer) | |
| A gelatin layer containing: | |
| Silver iodobromide emulsion (silver iodide: 6 mol %; mean grain size: 1.2 μm) | 1.0 g-Ag/m$^2$ |
| Sensitizing Dye G | 2.7 × 10$^{-4}$ mol per mol of Ag |
| Sensitizing Dye E | 1.1 × 10$^{-4}$ mol per mol of Ag |
| Coupler C-8 | 0.25 g/m$^2$ |
| Coupler C-3 | 0.013 g/m$^2$ |
| Coupler C-9 | 0.009 g/m$^2$ |
| Coupler C-10 | 0.011 g/m$^2$ |
| Ninth Layer: (Third Green-Sensitive Emulsion Layer) | |
| A gelatin layer containing: | |
| Silver iodobromide emulsion (silver iodide: 8 mol %; mean grain size: 1.8 μm) | 2.0 g-Ag/m$^2$ |
| Sensitizing Dye G | 3.0 × 10$^{-4}$ mol per mol of Ag |
| Sensitizing Dye E | 1.2 × 10$^{-4}$ mol per mol of Ag |
| Coupler C-3 | 0.008 g/m$^2$ |
| Coupler C-11 | 0.05 g/m$^2$ |
| Coupler C-17 | 0.001 g/m$^2$ |

| -continued | |
|---|---|
| Tenth Layer: (Yellow Filter Layer) | |
| A gelatin layer containing: | |
| Yellow colloidal silver | 0.04 g/m² |
| 2,5-Di-t-pentadecylhydroquinone | 0.031 g/m² |
| Eleventh Layer: (First Blue-Sensitive Emulsion Layer) | |
| A gelatin layer containing: | |
| Silver iodobromide emulsion (silver iodide: 5 mol %; mean grain size: 0.4 μm) | 0.32 g-Ag/m² |
| Coupler C-12 | 0.68 g/m² |
| Coupler C-13 | 0.03 g/m² |
| Coupler C-18 | 0.015 g/m² |
| Twelfth Layer: (Second Blue-Sensitive Emulsion Layer) | |
| A gelatin layer containing: | |
| Silver iodobromide emulsion (silver iodide: 10 mol %; mean grain size: 1.0 μm) | 0.29 g-Ag/m² |
| Sensitizing Dye F | $2.2 \times 10^{-4}$ mol per mol of Ag |
| Coupler C-12 | 0.22 g/m² |
| Thirteenth Layer: (Fine Grain Emulsion) | |
| A gelatin layer containing: | |
| Silver iodobromide emulsion (silver iodide: 2 mol %; mean grain size: 0.15 μm) | 0.4 g-Ag/m² |
| Fourteenth Layer: (Third Blue-Sensitive Emulsion Layer) | |
| A gelatin layer containing: | |
| Silver iodobromide emulsion (silver iodide: 14 mol %; mean grain size: 2.3 μm) | 0.79 g-Ag/m² |
| Sensitizing Dye F | $2.3 \times 10^{-4}$ mol per mol of Ag |
| Coupler C-12 | 0.19 g/m² |
| Coupler C-14 | 0.001 g/m² |
| Fifteenth Layer: (First Protective Layer) | |
| A gelatin layer containing: | |
| Ultraviolet Absorbent C-1 | 0.14 g/m² |
| Ultraviolet Absorbent C-2 | 0.22 g/m² |
| Sixteenth Layer: (Second Protective Layer) | |
| A gelatin layer containing: | |
| Polymethyl methacrylate particles (diameter: 1.5 μm) | 0.05 g/m² |

Each of the above layers additionally contained Gelatin Hardener C-15 and a surface active agent.

The resulting sample as designated as Sample No. 101.

The compounds used in Sample No. 101 are shown below.

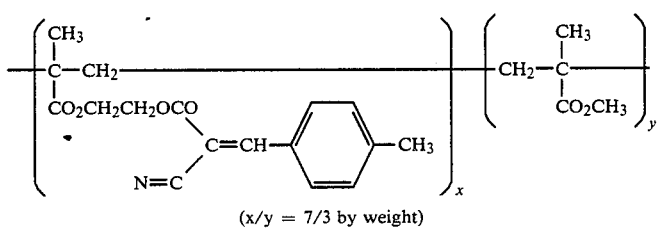

C-1

(x/y = 7/3 by weight)

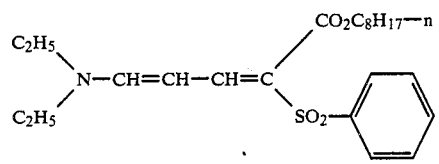

C-2

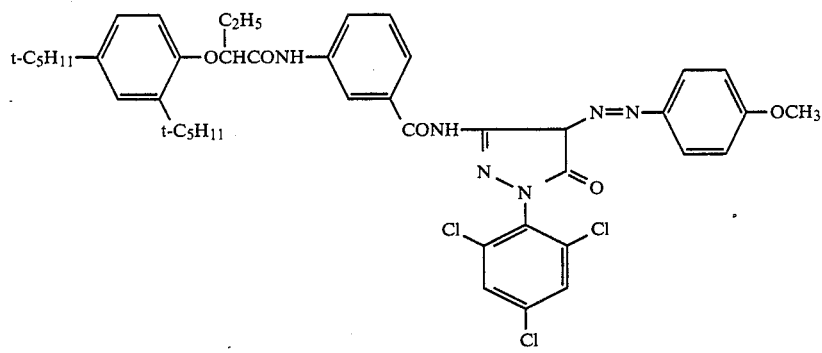

C-3

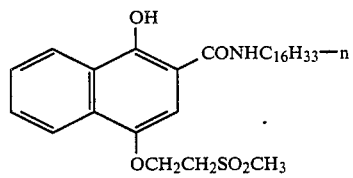

C-4

C-5
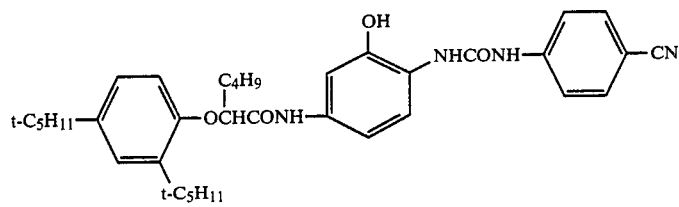
C-6
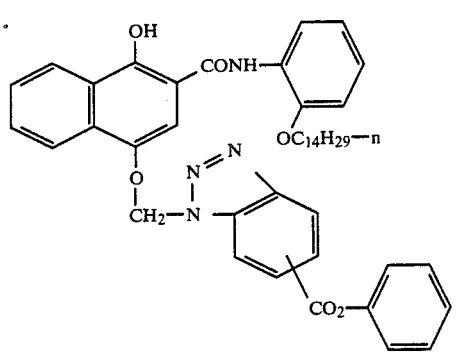
C-7
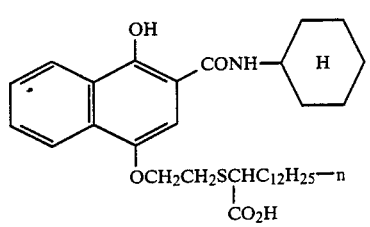
C-8
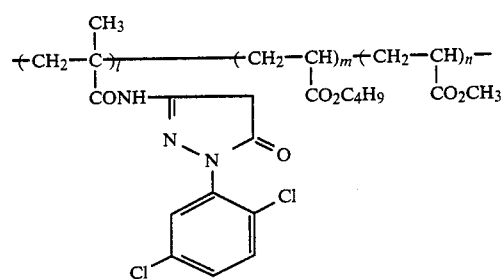
(l/m/n = 2/1/1 by weight)
C-9
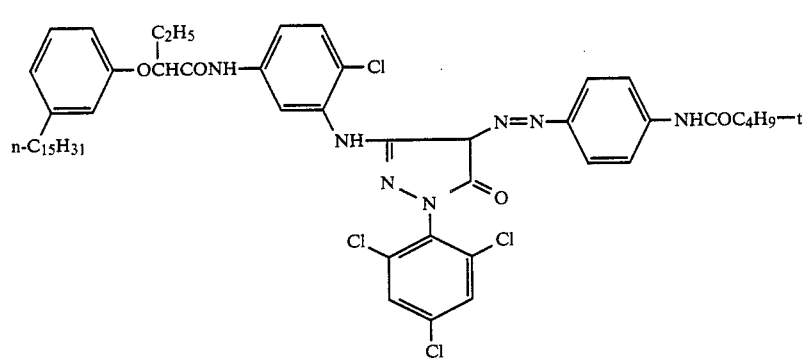

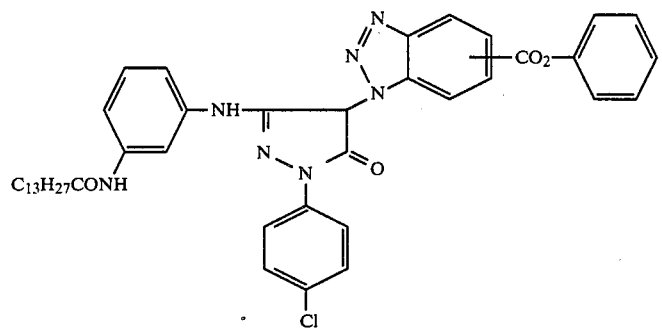
C-10
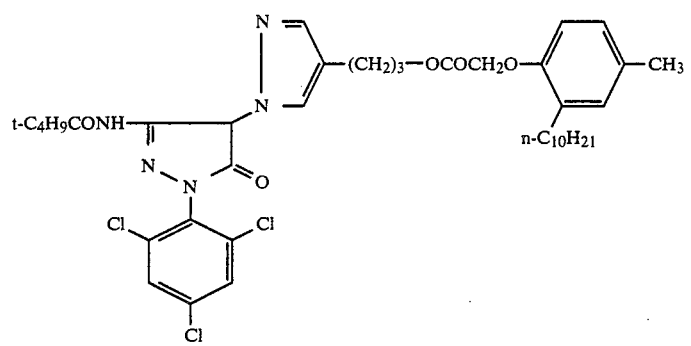
C-11
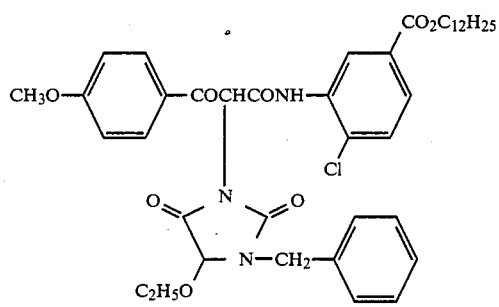
C-12
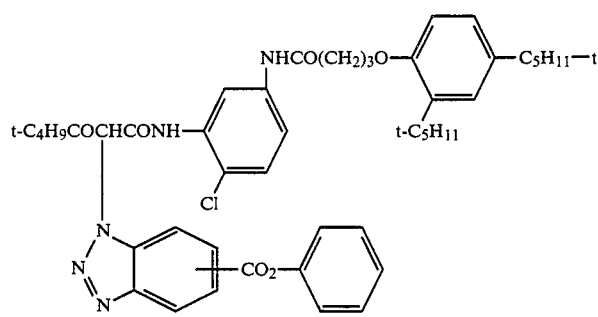
C-13
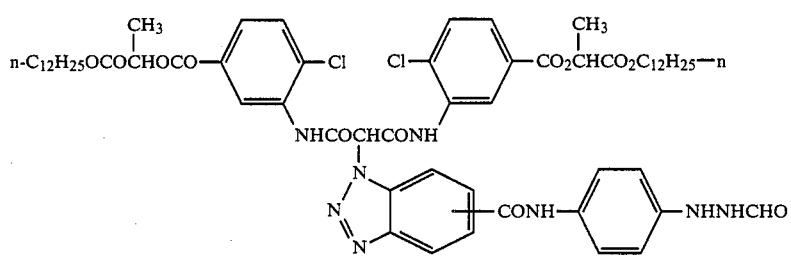
C-14
$CH_2=CHSO_2CH_2CONHCH_2CH_2NHCOCH_2SO_2CH=CH_2$  C-15

-continued
C-16
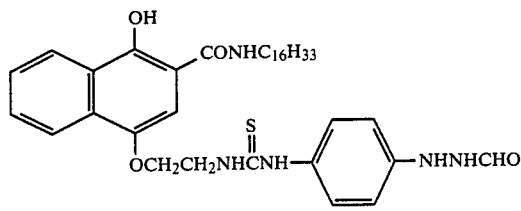
C-17
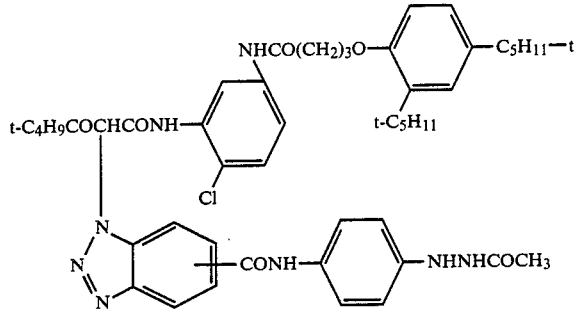
C-18
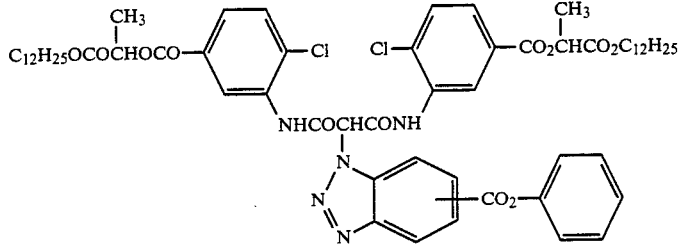
Sensitizing Dye A
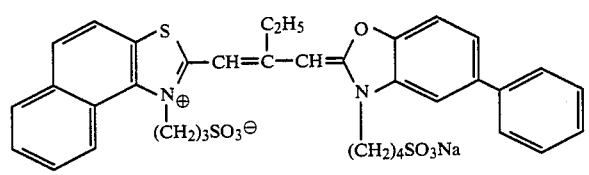
Sensitizing Dye B
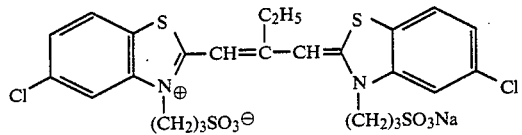
Sensitizing Dye C
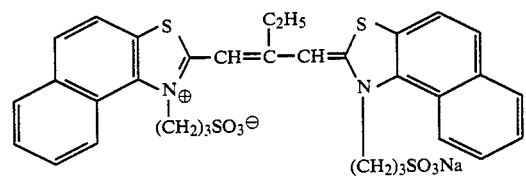
Sensitizing Dye D
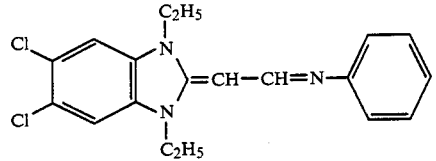
Sensitizing Dye E
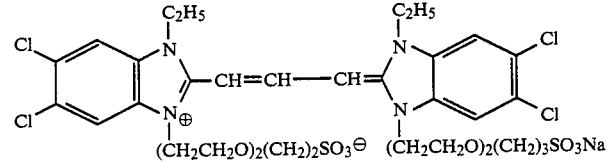
Sensitizing Dye F
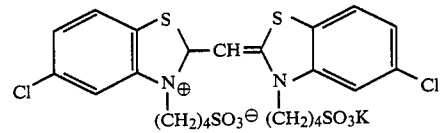
Sensitizing Dye G -continued

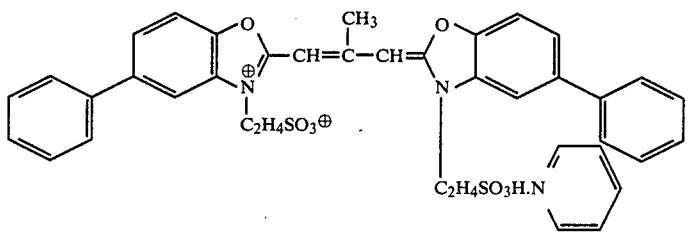

Sample Nos. 102 to 115 were prepared in the same manner as for Sample No. 101, except adding $0.5 \times 10^{-5}$ mol/m² of the compound shown in Table 1 to each of the fourth and fifth layers.

Each of Sample No. 101 to 115 thus prepared was exposed partly to red light and partly to white light (red+Green+blue light) through a step-wedge. The exposure amount of red light at the time of white light exposure and the exposure amount at the time of red light exposure were equal.

The thus exposed material was subjected to color development processing at 38° C. according to the procedure described below using the processing solutions described below.

Upon comparing the cyan image obtained by red light exposure and that obtained by white light exposure, a difference in exposure amount (ΔlogE) at the area having a cyan density of 0.6 was measured. The larger the ΔlogE, the greater are the interimage effects.

Separately, each Sample was exposed to light through a pattern for MTF (modulation transfer function) measurement, and submitted to the color development processing. The thus processed samples were measured with a microdensitometer, and MTF values of these samples were calculated. The "MTF value" is described in *Theory of the Photographic Process*, 4th edition, p. 604, Macmillan Publishing Co., Inc. (1977). Sharpness was represented by MTF value of 10 line/mm. Higher MTF value implies higher sharpness.

The results thus obtained are shown in Table 1.

| Color Development Processing: | |
|---|---|
| 1. Color development | 3'15" (' = min., " = sec.) |
| 2. Bleaching | 6'30" |
| 3. Washing | 3'15" |
| 4. Fixing | 6'30" |
| 5. Washing | 3'15" |
| 6. Stabilization | 3'15" |
| Color Developer: | |
| Sodium nitrilotriacetate | 1.0 g |
| Sodium sulfite | 4.0 g |
| Sodium carbonate | 30.0 g |
| Potassium bromide | 1.4 g |
| Hydroxylamine sulfate | 2.4 g |
| 4-(N—Ethyl-β-hydroxyethylamino)-2-methylaniline sulfate | 4.5 g |
| Water to make | 1 liter |
| Bleaching Solution: | |
| Ammonium bromide | 160.0 g |
| Aqueous ammonia (28%) | 25.0 ml |
| Sodium (ethylenediaminetetra-acetate)iron | 130.0 g |
| Glacial acetic acid | 14.0 ml |
| Water to make | 1 liter |
| Fixer: | |
| Sodium tetrapolyphosphate | 2.0 g |
| Sodium sulfite | 4.0 g |
| Ammonium thiosulfate (70%) | 175.0 ml |
| Sodium bisulfite | 4.6 g |
| Water to make | 1 liter |

| -continued | |
|---|---|
| Stabilizer: | |
| Formalin (37 wt % formaldehyde solution) | 8.0 ml |
| Water to make | 1 liter |

TABLE 1

| Sample No. | Additive | ΔlogE (D = 0.6) | MTF (10 line/mm) | Remark |
|---|---|---|---|---|
| 101 | — | 0.21 | 0.40 | Control |
| 102 | Compound A | 0.23 | 0.42 | Comparison |
| 103 | Compound B | 0.23 | 0.42 | " |
| 104 | Compound C | 0.24 | 0.43 | " |
| 105 | Compound D | 0.21 | 0.40 | " |
| 106 | (2) | 0.37 | 0.56 | Invention |
| 107 | (4) | 0.40 | 0.59 | " |
| 108 | (9) | 0.38 | 0.57 | " |
| 109 | (11) | 0.39 | 0.58 | " |
| 110 | (14) | 0.36 | 0.55 | " |
| 111 | (20) | 0.38 | 0.56 | " |
| 112 | (22) | 0.38 | 0.57 | " |
| 113 | (23) | 0.39 | 0.59 | " |
| 114 | (30) | 0.40 | 0.60 | " |
| 115 | (33) | 0.38 | 0.57 | " |

Note:
Compound A:

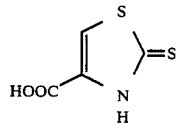

(disclosed in U.S. Pat. No. 3,536,486)
Compound B:

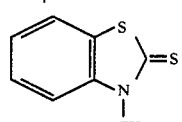

(disclosed in Japanese Patent Publication No. 34169/73)
Compound C:

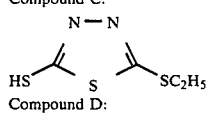

Compound D:

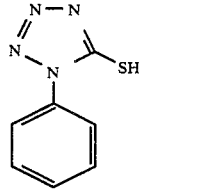

It can be seen from Table 1 above that the light-sensitive materials according to the present invention are superior to the comparative samples in terms of interimage effects and sharpness.

EXAMPLE 2

Sample No. 201 was pepared by coating the following layers on a cellulose triacetate film support in the order listed.

First Layer: (Antihalation Layer)

A gelatin layer containing black colloidal silver.

Second Layer: (Gelatin Intermediate Layer)

2,5-Di-t-octylhydroquinone was dissolved in 100 ml of dibutyl phthalate and 100 ml of ethyl acetate, and the solution was dispersed in 1 kg of a 10% gelatin aqueous solution under stirring at a high speed to prepare 2 kg of an emulsion. The emulsion was mixed with 1 kg of a fine grain silver iodobromide emulsion (silver iodide: 1 mol %; grain size: 0.6 μm) which had not been chemically sensitized and 1.5 kg of a 10% aqueous gelatin solution, and then the mixture was coated to a dry thickness of 2 μm (silver coverage: 0.4 g/m$^2$).

Third Layer: (Low-Sensitive Red-Sensitive Emulsion Layer)

In 100 ml of tricresyl phosphate and 100 ml of ethyl acetate was dissolved 100 g of a cyan coupler, 2-(heptafluorobutylamido)-5-[2'-(2''',4''-di-t-aminophenoxy)-butylamido]-phenol, and the solution was dispersed in 1 kg of a 10% aqueous gelatin solution under stirring at high speed to obtain 500 g of an emulsion. The emulsion was mixed with 1 kg of a red-sensitive silver iodobromide emulsion (silver content: 70 g; gelatin content: 60 g; iodine content: 4 mol %), and the mixture was coated to a dry thickness of 1 μm (silver coverage: 0.5 g/m$^2$).

Fourth Layer: (High-Sensitive Red-Sensitive Emulsion Layer)

In 100 ml of tricresyl phosphate and 100 ml of ethyl acetate was dissolved a cyan coupler, 2-(heptafluorobutylamido)-5-[2'-(2''',4''-di-t-aminophenoxy)-butylamido]-phenol, and the solution was dispersed in 1 kg of a 10% gelatin aqueous solution by stirring at a high speed to obtain 1 kg of an emulsion. The resulting emulsion was mixed with 1 kg of a red-sensitive silver iodobromide emulsion (silver content: 70 g; gelatin content: 60 g; iodide content: 2.5 mol %), and the composition was coated to a dry thickness of 2.5 μm (silver coverage: 0.7 g/m$^2$).

Fifth Layer: (Intermediate Layer)

100 ml of 2,5-di-t-octylhydroquinone was dissolved in 100 ml of dibutyl phthalate and 100 ml of ethyl acetate, and the solution was dispersed in 1 kg of a 10% gelatin aqueous solution by stirring at a high speed to prepare 1 kg of an emulsion. The emulsion was mixed with 1 kg of a 10% gelatin aqueous solution, and the resulting composition was coated to a dry thickness of 1 μm.

Sixth Layer: (Low-Sensitive Green-Sensitive Emulsion Layer)

An emulsion was prepared in the same manner as for the emulsion of the third layer, except for using a magenta coupler, 1-(2',4',6'-trichlorophenyl)-3-[3'''-(2''',4'''-di-t-amylphenoxyacetamido)benzamido]-5-pyrazolone, in place of the cyan coupler. 300 g of the emulsion was mixed with 1 kg of a green-sensitive silver iodobromide emulsion (silver content: 70 g; gelatin content: 60 g; iodide content: 3 mol %), and the resulting composition was coated to a dry thickness of 1.3 μm (silver coverage: 0.7 g/m$^2$).

Seventh Layer: (High-Sensitive Green-Sensitive Emulsion Layer)

An emulsion was prepared in the same manner as for the emulsion for the third layer except for using a magenta coupler, 1-(2',4',6'-trichlorophenyl)-3-[3''(2''',4'''-di-t-amylphenoxyacetamido)benzamido]-5-pyrazolone, in place of the cyan coupler. 1 kg of this emulsion was mixed with 1 kg of a green-sensitive silver iodobromide emulsion (silver content: 70 g; gelatin content: 60 g; iodide content: 2.5 mol %), and the resulting composition was coated to a dry thickness of 3.5 μm (silver coverage: 0.8 g/m$^2$).

Eighth Layer: (Yellow Filter Layer)

An emulsion containing yellow colloidal silver was coated to a dry thickness of 1 μm.

Ninth Layer: (Low-Sensitive Blue-Sensitive Emulsion Layer)

An emulsion was prepared in the same manner as for the emulsion of the third layer, except for using a yellow coupler, α-(pivaloyl)-α-(1-benzyl-5-ethoxy-3-hydantoinyl)-2-chloro-5-dodecyloxycarbonylacetanilide, in place of the cyan coupler. 1 kg of this emulsion was mixed with 1 kg of a blue-sensitive silver iodobromide emulsion (silver content: 70 g; gelatin content: 60 g; iodide content: 2.5 mol %), and the resulting composition was coated to a dry thickness of 1.5 μm (silver coverage: 0.6 g/m$^2$).

Tenth Layer: (High-Sensitive Blue-Sensitive Emulsion Layer)

An emulsion was prepared in the same manner as for the emulsion of the third layer, except for using a yellow coupler, α-(pivaloyl)-α-(1-benzyl-5-ethoxy-3-hydantoinyl)-2-chloro-5-dodecyloxycarbonylacetanilide, in place of the cyan coupler. 1 kg of this emulsion was mixed with 1 kg of a silver iodobromide emulsion (silver content: 70 g; gelatin content: 60 g; iodide content: 2.5 mol %), and the resulting composition was coated to a dry thickness of 3 μm (silver coverage: 1.1 g/m$^2$).

Eleventh Layer: (Second Protective Layer)

1 kg of a dispersion of Ultraviclet Absorbent C-1 as used in Example 1 was mixed with 1 kg of a 10% gelatin aqueous solution, and the resulting composition was coated to a dry thickness of 2 μm.

Twelfth Layer: (First Protective Layer)

A 10% gelatin aqueous solution containing polymethyl methacrylate particles having a diameter of 1.5 μm was coated to a dry thickness of 0.8 μm.

Each of these layers further contained Gelatin Hardener C-15 and a surface active agent in addition to the above-described components.

Sample Nos. 202 to 216 were prepared in the same manner as for Sample No.201 except that a compound shown in Table 2 was added to the layers indicated in Table 2 in an amount of $1 \times 10^{-5}$ mol/m$^2$ per layer.

Each of the resulting samples (Sample Nos. 201 to 216) was exposed partly to red light, green light, blue light or white light (red+green+blue light) through a step-wedge. The exposure amounts of the red light, green light and blue light in the white light exposure were equal to the exposure amounts in the red light exposure, green light exposure and blue light exposure, respectively.

The exposed sample was then subjected to the following development processing using the following 5 processing solutions.

| Development Processing: | | |
|---|---|---|
| Step | Time | Temperature |
| First Development | 6 mins. | 38° C. |
| Washing | 2 mins. | " |
| Reversing | 2 mins. | " |
| Color Development | 6 mins. | " |
| Compensation | 2 mins. | " |
| Bleaching | 6 mins. | " |
| Fixing | 4 mins. | " |
| Washing | 4 mins. | " |
| Stabilization | 1 min. | room temperature |
| Drying | | |

| First Developer: | |
|---|---|
| Water | 700 ml |
| Pentasodium nitrilo-N,N,N—trimethylenephosphonate | 3 g |
| Sodium sulfite | 20 g |
| Hydroquinone monosulfonate | 30 g |
| Sodium carbonate monohydrate | 30 g |
| 1-Phenyl-4-methyl-4-hydroxymethyl-3-pyrazolidone | 2 g |
| Potassium bromide | 2.5 g |
| Potassium thiocyanate | 1.2 g |
| Potassium iodide (0.1% solution) | 2 ml |
| Water to make | 1000 ml |
| Reversing Solution: | |
| Water | 700 ml |
| Pentasodium nitrilo-N,N,N—trimethylenephosphonate | 3 g |
| Stannous chloride dihydrate | 1 g |
| p-Aminophenol | 0.1 g |
| Sodium hydroxide | 8 g |
| Glacial acetic acid | 15 ml |
| Water to make | 1000 ml |
| Color Developer: | |
| Water | 700 ml |
| Pentasodium nitrilo-N,N,N—trimethylenephosphonate | 3 g |
| Sodium sulfite | 7 g |
| Sodium tertiary phosphate dodecahydrate | 36 g |
| Potassium bromide | 1 g |
| Potassium iodide (0.1% solution) | 90 ml |
| Sodium hydroxide | 3 g |
| Citrazinic acid | 1.5 g |
| N—Ethyl-N—(β-methanesulfonamidoethyl)-3-methyl-4-aminoaniline sulfate | 11 g |
| Ethylenediamine | 3 g |
| Water to make | 1000 ml |

| Development Processing: | |
|---|---|
| Compensating Solution: | |
| Water | 700 ml |
| Sodium sulfite | 12 g |
| Sodium ethylenediaminetetraacetate dihydrate | 8 g |
| Thioglycerin | 0.4 ml |
| Glacial acetic acid | 3 ml |
| Water to make | 1000 ml |
| Bleaching Solution: | |
| Water | 800 ml |
| Sodium ethylenediaminetetraacetate dihydrate | 2 g |
| Ammonium (ethylenediaminetetraacetato)-iron(III) dihydrate | 120 g |
| Potassium bromide | 100 g |
| Water to make | 1000 ml |
| Fixing Solution: | |
| Water | 800 ml |
| Sodium thiosulfate | 80.0 g |
| Sodium sulfite | 5.0 g |
| Sodium bisulfite | 5.0 g |
| Water to make | 1000 ml |
| Stabilizing Solution: | |
| Water | 800 ml |
| Formalin | 5.0 ml |
| Fuji Dry Well (surface active agent produced by Fuji Photo Film Co., Ltd.) | 5.0 ml |
| Water to make | 1000 ml |

Upon comparing the cyan image obtained by red light exposure and that obtained by white light exposure, a difference in exposure amount ($\Delta \log E$) at the area having a cyan density of 1.0 was measured. In the same manner, $\Delta \log E$ in the case of green light exposure and blue light exposure was also measured.

The results obtained are shown in Table 2 below.

TABLE 2

| Sample No. | Additive | Layer for Additive | $\Delta \log E$ (Cyan Density = 1.0) | $\Delta \log E$ (Magenta Density = 1.0) | $\Delta \log E$ (Yellow Density = 1.0) | Remark |
|---|---|---|---|---|---|---|
| 201 | — | — | 0.25 | 0.15 | 0.10 | Comparison |
| 202 | Compound A | 3rd, 6th, 9th | 0.28 | 0.17 | 0.12 | " |
| 203 | Compound B | " | 0.29 | 0.18 | 0.13 | " |
| 204 | Compound C | " | 0.29 | 0.18 | 0.12 | " |
| 205 | (4) | " | 0.47 | 0.33 | 0.30 | Invention |
| 206 | (8) | " | 0.44 | 0.30 | 0.27 | " |
| 207 | (11) | " | 0.46 | 0.31 | 0.28 | " |
| 208 | (24) | " | 0.46 | 0.32 | 0.28 | " |
| 209 | (25) | " | 0.45 | 0.30 | 0.27 | " |
| 210 | (28) | " | 0.46 | 0.32 | 0.28 | " |
| 211 | (30) | " | 0.47 | 0.33 | 0.31 | " |
| 212 | (35) | " | 0.46 | 0.32 | 0.29 | " |
| 213 | (41) | " | 0.46 | 0.31 | 0.29 | " |
| 214 | (4) | 2nd, 5th, 8th | 0.41 | 0.28 | 0.23 | " |
| 215 | (4) | 2nd, 6th, 9th | 0.42 | 0.32 | 0.28 | " |
| 216 | (4) | 4th, 7th, 10th | 0.40 | 0.27 | 0.24 | " |

Note: Compounds A, B and C are the same as used in Example 1.

It can be seen from the results of Table 2 that the interimage effects obtained by the present invention are far greater than those obtained in the comparative samples.

EXAMPLE 3

Onto a cellulose triacetate film support were coated the following layers in the order listed, to prepare a black-and-white photographic light-sensitive material.

First Layer: (Low-Sensitive Silver Halide Emulsion Layer)

Potassium bromide, potassium iodide and silver nitrate were added to a gelatin aqueous solution while vigorously stirring to prepare a silver iodobromide emulsion (silver iodide content: 3 mol %) having a mean grain size of 0.6 μm. After desalting, the emulsion was subjected to gold-sulfur sensitization using chloroauric acid and sodium thiosulfate to the optimum degree to prepare Emulsion A. Emulsion A was coated to the support to provide a silver coverage of 1 g/m².

Second Layer: (High-Sensitive Silver Halide Emulsion Layer)

Emulsion B which was prepared in the same manner as for Emulsion A but having a mean grain size of 1.2 μm was coated to provide a silver coverage of 2.5 g/m².

Third Layer: (Protective Layer)

A layer containing 1.3 g/m² of gelatin and 0.05 g/m² of polymethyl methacrylate particles having a diameter of 1.5 μm.

Each of the layers further contained Gelatin Hardener C-15, a surface active agent and sodium polystyrenesulfonate as a thickener in addition to the above-described components. The thus prepared material was designated as Sample No. 301.

Sample Nos. 302 to 314 were prepared in the same manner as for Sample No. 301 except that each of the layers indicated in Table 3 further contained the compound indicated in Table 3 in an amount of $0.3 \times 10^{-5}$ mol/m² per layer.

Each sample was exposed to light through a pattern for granularity measurement or MTF measurement and then subjected to black-and-white development at 20° C. for 7 minutes using the following processing solutions.

| Developer: | |
|---|---|
| Metol (p-(N—methylamino)phenol sulfate) | 2 g |
| Sodium sulfite | 100 g |
| Hydroquinone | 5 g |
| Borax.5H₂O | 1.53 g |
| Water to make | 1000 ml |
| Fixing Solution: | |
| Ammonium thiosulfate | 200.0 g |
| Anhydrous sodium sulfite | 20.0 g |
| Boric acid | 8.0 g |
| Disodium ethylenediaminetetraacetate | 0.1 g |
| Aluminum sulfate | 15.0 g |
| Sulfuric acid | 2.0 g |
| Glacial acetic acid | 22.0 g |
| Water to make | 1000 ml |
|  | (pH 4.2) |

The thus processed samples were examined for RMS granularity through the density measurement using a microdensitometer, according to *Photographic Science and Engineering*, vol. 19, p. 235 (1975). That is, graininess (RMS granularity) of the resulting image was determined by scanning the image with a microdensitometer and multiplying a standard deviation in density variation by 1000. The smaller the RMS granularity the better is the graininess.

Further, sharpness of the image was evaluated in terms of the MTF value as in Example 1.

These results are shown in Table 3.

TABLE 3

| Sample No. | Additive | Layers for Additive | RMS Granularity (D = 1.5) | MTF Value (10 line/mm) | Remarks |
|---|---|---|---|---|---|
| 301 | — | — | 28 | 0.88 | Comparison |
| 302 | Compound A | 1th, 2nd | 27 | 0.89 | Comparison |
| 303 | Compound B | " | 27 | 0.90 | Comparison |
| 304 | Compound C | " | 27 | 0.89 | Comparison |
| 305 | (1) | " | 22 | 0.96 | Invention |
| 306 | (6) | " | 21 | 0.98 | " |
| 307 | (7) | " | 22 | 0.95 | " |
| 308 | (9) | " | 21 | 0.98 | " |
| 309 | (11) | " | 21 | 0.97 | " |
| 310 | (22) | " | 21 | 0.98 | " |
| 311 | (26) | " | 22 | 0.97 | " |
| 312 | (40) | " | 23 | 0.96 | " |
| 313 | (1) | 2nd, 3rd | 25 | 0.94 | " |
| 314 | (6) | " | 25 | 0.94 | " |

Note: Compounds A, B and C are the same as used in Example 1.
The additive was added during the formation of silver halide particles in preparation of Emulsions A and B, and the thus obtain emulsions were coated to form the 1st and 2nd layers, respectively. Further, the 3rd layer of Sample Nos. 313 and 314 was formed by adding the additive during preparation of the coating composition.

As is shown in Table 3, the light-sensitive materials according to the present invention have improved graininess and sharpness as compared with the comparative samples.

While the invention has been described in detail and with reference to specific embodiments thereof, it will be apparent to one skilled in the art that various changes and modifications can be made therein without departing from the spirit and scope thereof.

What is claimed is:

1. A silver halide photographic material comprising at lest one compound represented by formula (I) or formula (II)

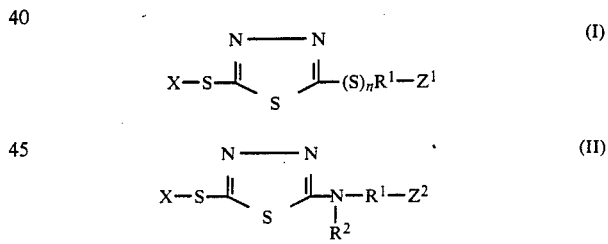

wherein $R^1$ represents a straight or branched chain alkylene, alkenylene or aralkylene group, or an arylene group; $R^2$ represents a hydrogen atom, or a substituted or unsubstituted alkyl, aryl, alkenyl or aralkyl group; X represents a hydrogen atom, an alkali metal atom, an ammonium group, or a precursor capable of providing a hydrogen atom or an alkali metal atom under an alkaline condition; $Z^1$ and $Z^2$ each represents a polar substituent, wherein $Z^1$ represents a quaternary ammonium group, an alkoxy group, an alkylthio group, an arylthio group, a heterocyclic oxy group, a carbamoyl group, a sulfamoyl group, an acyloxy group, a ureido group, a thioureido group, or a sulfonyloxy group; and $Z^2$ represents a quaternary ammonium group, an alkoxy group, an alkylthio group, an arylthio group, a heterocyclic oxy group, a heterocyclic thio group, a carbamoyl group, a sulfamoyl group, an acyloxy group, a ureido group, a thioureido group, a sulfonyloxy group, a substituted or unsubstituted amino group or a salt thereof, an aryloxy group, a heterocyclic group or a cyano group; and n represents 0 or 1.

2. A silver halide photographic material as in claim 1, wherein $R^1$ represents an alkylene group.

3. A silver halide photographic material as in claim 1, wherein $R^2$ represent a hydrogen atom, or an alkyl group.

4. A silver halide photographic material as in claim 1, wherein $Z^1$ represents a quaternary ammonium group, a carbamoyl group, or a ureido group; and $Z^2$ represents a quaternary ammonium group, a carbamoyl group, a ureido group, an amino group, or a heterocyclic group.

5. A silver halide photographic material as in claim 1, wherein n in formula (I) represents 1.

6. A silver halide photographic material as in claim 1, wherein said compound is represented by formula (I).

7. A silver halide photographic material as in claim 1, wherein said compound is represented by formula (II).

8. A silver halide photographic material as in claim 1, wherein said compound is present in an amount of from $10^{-1}$ to $10^{-5}$ mols per mol of silver halide in the later in which the compound is incorporated or in layer adjacent thereof when silver halide is not contained in the layer in which said compound is incorporated.

9. A silver halide photographic light-sensitive material as in claim 1, wherein said compound is present in an amount of from $3 \times 10^{-2}$ to $3 \times 10^{-4}$ mols per mol of silver halide in the layer in which the compound is incorporated or in layers adjacent thereto.

10. A silver halide photographic material as in claim 1, wherein said material is a multi-layer color photographic light-sensitive material comprising at least one silver halide emulsion layer and said compound is present in at least one silver halide emulsion layer or a layer adjacent thereto.

11. A silver halide photographic material as in claim 1, wherein said material is a black-and-white photographic light-sensitive material comprising at least one silver halide emulsion layer, and said compound is present in at least one silver halide emulsion layer or a layer adjacent thereto.

* * * * *